United States Patent [19]
Nemori et al.

[11] Patent Number: 5,015,387
[45] Date of Patent: May 14, 1991

[54] METHOD FOR ACTIVATING CELLULOSIC MEMBRANE, ACTIVATED CELLULOSIC MEMBRANE, METHOD OF FIXING PHYSIOLOGICALLY ACTIVE SUBSTANCE ON THE ACTIVATED CELLULOSIC MEMBRANE AND PHYSIOLOGICALLY ACTIVE SUBSTANCE-FIXED MEMBRANE

[75] Inventors: Ryoichi Nemori; Yoshihisa Tsukada, both of Kanagawa, Japan

[73] Assignee: Fuji Photo Film Co., Ltd., Kanagawa, Japan

[21] Appl. No.: 423,322

[22] Filed: Oct. 18, 1989

[30] Foreign Application Priority Data

Oct. 18, 1988 [JP] Japan .................................. 63-262202
Nov. 8, 1988 [JP] Japan .................................. 63-281850
Nov. 17, 1988 [JP] Japan .................................. 63-290614

[51] Int. Cl.$^5$ ............................................. B01D 71/10
[52] U.S. Cl. .................................... 210/638; 210/655; 210/500.29

[58] Field of Search ................ 556/419, 421; 427/245; 210/634, 638, 644, 645, 646, 647, 649–655, 500.29, 500.3, 500.31, 500.32

[56] References Cited

U.S. PATENT DOCUMENTS 4,801,726  1/1989  Glese et al. ...................... 556/419

Primary Examiner—Frank Sever
Attorney, Agent, or Firm—Sughrue, Mion, Zinn, Macpeak & Seas

[57] ABSTRACT

A method for activating a membrane comprising cellulose as a main component, by reacting the membrane with a compound of the formula $Cl-SO_2-R$ or $Cl-CO-R_1$ where R is an optionally substituted alkyl or phenyl group and $R_1$ is a releasing group, an activated membrane obtained by the method, a method of fixing a physiologically active substance on the activated membrane and a physiologically active substance-fixed membrane obtained by the method. A physiologically active substance can be fixed on the activated membrane by stable chemical bond between the substance and the membrane while maintaining the physiological activity of the substance.

13 Claims, No Drawings

METHOD FOR ACTIVATING CELLULOSIC MEMBRANE, ACTIVATED CELLULOSIC MEMBRANE, METHOD OF FIXING PHYSIOLOGICALLY ACTIVE SUBSTANCE ON THE ACTIVATED CELLULOSIC MEMBRANE AND PHYSIOLOGICALLY ACTIVE SUBSTANCE-FIXED MEMBRANE

FIELD OF THE INVENTION

The present invention relates to a method of activating a membrane comprising, as a main component, cellulose (hereinafter referred to as a "cellulosic membrane") so that it is reactive with a physiologically active substance and to an activated cellulosic membrane prepared by this method. Moreover, the present invention relates to a method of fixing a physiologically active substance to the activated cellulosic membrane and to a physiologically active substance-fixed membrane prepared by the fixation method.

BACKGROUND OF THE INVENTION

A fixed physiologically active substance obtained by fixing a physiologically active substance, such as an enzyme, a coenzyme, a hormone, a receptor or an inhibitor to an insoluble carrier is widely utilized as a material for a bioreactor, a biosensor or affinity chromatography for preparation of chemical agents, foods and medicines as well as for clinical diagnosis or therapy. In this case, the fixed physiologically active substance may be in the form of either granules or membranes, both of which are being studied by many researchers in various groups.

The form of a fixed physiologically active substance to a porous granular carrier has been studied to the greatest extent, but it has been pointed out that the efficacy of the fixed physiologically active substance is reduced because of the restricted diffusibility caused by the non-stirring layer in the inside and periphery of the grain and, as the case may be, only a small part of the latent activity of the fixed substance can often be utilized in the fixed system. (For instance, see JP-B-58-35679. The term "JP-B" as used herein means an "examined published Japanese patent publication".) In order to overcome this defect, a reaction method has been developed where an enzyme or the like is fixed to a fine porous membrane and the membrane is permeated with an aqueous substrate solution under pressure.

For the purpose of widely employing such a membrane-fixed physiologically active substance to a bioreactor, a biosensor, a material for affinity chromatography, clinical diagnosis and the like, it is important for the non-specific interaction between the membrane carrier and the protein to be as small as possible. Therefore, polysaccharides such as cellulose and the like, which have a high hydrophilicity but are not electrically charged, are preferred as the material for the membrane carrier.

Some methods were already known for fixing an enzyme or other physiologically active substance to a cellulosic membrane by chemical bonding. For instance, JP-A-56-97235 (the term "JP-A" as used herein means an "unexamined published Japanese patent application"), JP-B-58-44357 and JP-B-62-32919 disclose a method of activating a cellulosic membrane with an oxidizing agent and then fixing an enzyme to the thus-activated membrane. British Patent No. 1,183,260 discloses a method of activating cellulose or a like membrane with a triazine derivative and then fixing an enzyme to the thus activated membrane.

In these known methods, a physiologically active substance-fixed cellulosic membrane could be obtained. However, these known methods still have some problems and are not satisfactory for practical use. Specifically, in the activation method using an oxidizing agent, it is considered that the aldehyde group formed on the carrier reacts essentially with an amino group in the physiologically active substance to form a Schiff base whereby the physiologically active substance is fixed to the carrier. However, the Schiff base formed is not stable so that the fixed physiologically active substance is often released from the carrier. Where a reducing agent such as $NaBH_4$ or $NaBH_3CN$ is to be used for the purpose of preventing the release of the fixed physiologically active substance, the physiological activity of the substance is lowered by the treatment with such reducing agent. As a means of omitting the second stage reaction, such as a reduction, after the fixation of the physiologically active substance, a method of fixing a physiologically active substance with a triazine derivative has been developed. According to the method, however, the fixation reaction speed is slow and a relatively long period of time is required for the fixation. Therefore, when a physiologically active substance which is unstable is to be fixed using this method, deactivation of the substance during the course of the fixation is a serious problem.

British Patent No. 1,183,260 indicates activation of a membrane carrier (such as filter paper or cotton fabric) with a triazine derivative where the membrane is immersed in an alkali substance. However, where the method is applied to an asymmetric membrane made of fine fibers, for example, a cellulosic asymmetric membrane (such as a microfilter), the membrane is noticeably deformed probably because of hydrolysis of cellulose and the strength of the membrane is decreased. This is a serious difficulty.

As a result, development of a method of activating a cellulosic membrane without decreasing the properties of the membrane itself, as well as a method of fixing a physiologically active substance to the cellulosic membrane thus activated so that it has high reactivity with protein is desired.

SUMMARY OF THE INVENTION

One object of the present invention is to provide a method of activating a membrane comprising cellulose as a main component, especially an asymmetric membrane with excellent characteristics as to fluids so that it is active to a physiologically active substance and to provide the so activated membrane.

Another object of the present invention is to provide a method of fixing a physiologically active substance to the activated membrane with a stable chemical bond between the physiologically active substance and the membrane while maintaining the physiological activity of the substance as much as possible, as well as to provide the physiologically active substance-fixed membrane obtainable by this method.

These objects of the present invention are achieved by a method of activating a membrane comprising, as a main component, cellulose (a "cellulosic membrane") comprising reacting the membrane with a compound represented by the following formula (I) or (II):

$$Cl-SO_2-R \quad (I)$$

where R represents an optionally substituted alkyl group or an optionally substituted phenyl group, $$Cl-\overset{O}{\underset{\|}{C}}-R_1 \quad (II)$$

where $R_1$ represents a releasing group.

In one embodiment, the present invention provides a cellulosic membrane activated by this method.

In another embodiment, the present invention also provides a method of fixing a physiologically active substance to the activated cellulosic membrane by reacting the substance and the membrane.

In still another embodiment, the present invention further provides a physiologically active substance-fixed cellulosic membrane prepared by the fixing method.

DETAILED DESCRIPTION OF THE INVENTION

The membrane for use in the present invention may be any membrane comprising cellulose as a main component but is not specifically limited. Especially preferably, the membrane is an asymmetric one with a flat or hollow shape, which has a dense surface layer on one side of the membrane and has a relatively rough porous layer on the other side thereof. More specifically, a porous membrane having a pore diameter of from $0.1\mu$ to $10\mu$ (for example, a microfilter) as well as a so-called ultrafilter membrane having an even smaller pore diameter of from 1,000 to 1,000,000 for fractionating by molecular weight are preferably employed in the present invention. Methods of preparing such membranes are disclosed in, for example, JP-B-45-4663, JP-B-62-15642 and JP-B-62-34845. The thickness of the membrane (or the thickness of the wall for a hollow membrane) which is preferably employed in the present invention is $10\mu$ or more, more preferably from $10\mu$ to $300\mu$.

The optionally substituted alkyl group for R in the formula (I) contains from 1 to 20 carbon atoms, preferably from 1 to 13 carbon atoms and includes methyl, ethyl, propyl and 2,2,2-trifluoroethyl groups, and it is especially preferably a methyl group or a 2,2,2-trifluoroethyl group. The optionally substituted phenyl group for R in the formula (I) includes phenyl, p-methylphenyl, p-chlorophenyl and p-methoxyphenyl groups, and it is especially preferably a p-methylphenyl group.

More precisely, the compounds of the formula (II) are represented by the following formulae (III) and (IV):

$$Cl-\overset{O}{\underset{\|}{C}}-OR_2 \quad (III)$$

$$Cl-\overset{O}{\underset{\|}{C}}-N\diagup\!\!\!\diagdown X \quad (IV)$$

In the formula (III), $R_2$ represents a group capable of being released as $\ominus OR_2$. In the formula (IV), X represents a non-metallic atomic group for forming a 5-membered or 6-membered ring together with the nitrogen atom.

$R_2$ in the formula (III) represents an optionally substituted alkyl, aryl or heterocyclic group.

The alkyl group for $R_2$ is preferably an alkyl group having from 1 to 20, preferably from 1 to 13, carbon atoms and may be primary, secondary and tertiary alkyl groups. Further, it may form a ring including a condensed ring. Preferred examples of substituents for the alkyl group are a phenyl group and a halogen atom.

The aryl group for $R_2$ is preferably an optionally substituted phenyl group. Suitable substituents for the aryl group are, preferably, a nitro group, a cyano group, a sulfamoyl group, a carbamoyl group, an alkyloxycarbonyl group, an acyl group, a sulfonyl group, a fluorine atom and a chlorine atom. Two or more of these substituents may be present on the phenyl group. More preferably, the optionally substituted phenyl group is an unsubstituted phenyl group and a phenyl group substituted with a nitro group, a cyano group, an acyl group, a sulfonyl group, a fluorine atom or a chlorine atom.

Suitable examples of heterocyclic groups for $R_2$ are a succinic acid imide residue, a phthalic acid imide residue, a triazole residue, a benzotriazole residue and a tetrazole residue, each of which may be substituted. More preferably, the group includes a succinic acid imide residue, a phthalic acid imide residue and a benzotriazole residue, each of which may be substituted.

Examples of 5-membered or 6-membered rings formed by the nitrogen atom and X in the formula (IV) are a pyrrole residue, a pyrrolidine residue, a succinic acid imide residue, an imidazole residue, a pyrazole residue, a triazole residue, a tetrazole residue, a benzimidazole residue, a benzotriazole residue, an oxazolin-2-one residue, a thiazoline-2-thione residue, a piperidine residue, a uracil residue, a 2-pyridone residue and a 4-pyridone residue, each of which may be substituted. X is more preferably a non-metallic atomic group forming a 5-membered ring. Suitable examples of 5-membered rings formed by the nitrogen atom and X in the formula (IV) are a pyrrolidine residue, a pyrazole residue, an imidazole residue and a thiazolin-2-thione residue, each of which may be substituted.

Specific examples of compounds of the formulae (I) and (II) are described below, which, however, are not to be construed as limiting the present invention. Among them, Compounds (10), (21), (25), (47) and (48) are preferred.

$$Cl-\overset{O}{\underset{\|}{C}}-OCH_3 \quad (1)$$

$$Cl-\overset{O}{\underset{\|}{C}}-OCH_2CCl_3 \quad (2)$$

$$Cl-\overset{O}{\underset{\|}{C}}-OC_4H_9^{(n)} \quad (3)$$

$$Cl-\overset{O}{\underset{\|}{C}}-O-\overset{CH_3}{\underset{CH_3}{\overset{|}{C}}}-CH_3 \quad (4)$$

$$Cl-\overset{O}{\underset{\|}{C}}-OCF_2CF_3 \quad (5)$$

-continued
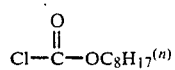 (6)
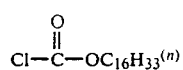 (7)
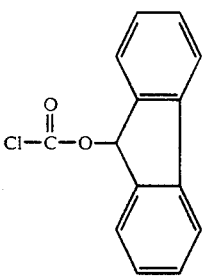 (8)
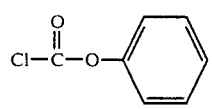 (9)
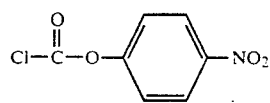 (10)
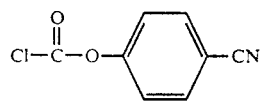 (11)
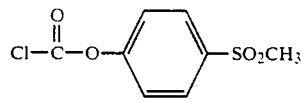 (12)
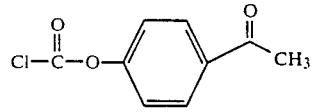 (13)
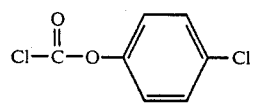 (14)
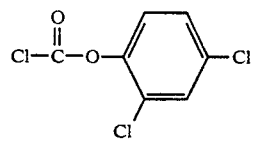 (15)
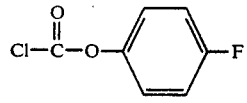 (16)
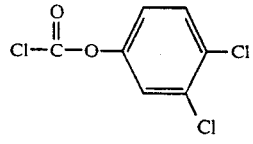 (17)
-continued
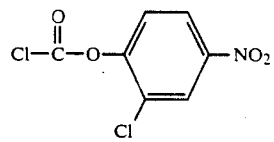 (18)
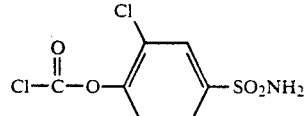 (19)
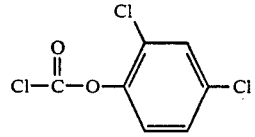 (20)
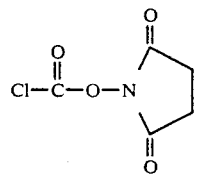 (21)
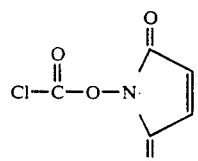 (22)
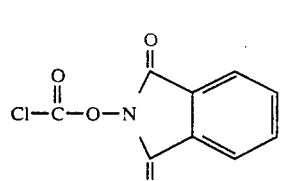 (23)
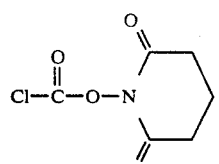 (24)
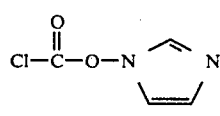 (25)
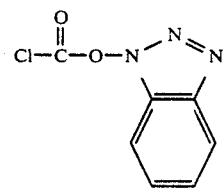 (26)
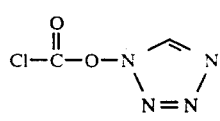 (27)

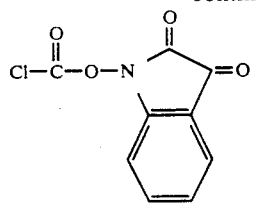
(28)

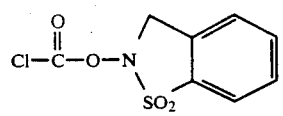
(29)

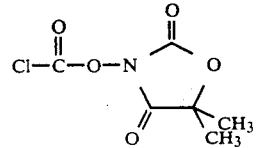
(30)

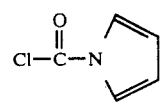
(31)

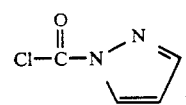
(32)

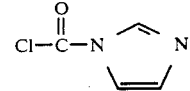
(33)

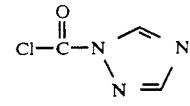
(34)

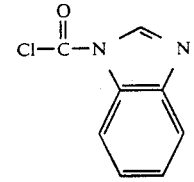
(35)

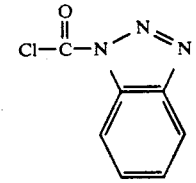
(36)

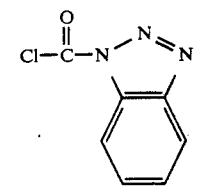
(37)

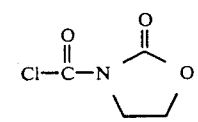
(38)

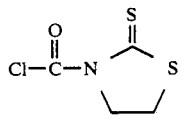
(39)

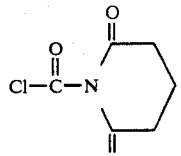
(40)

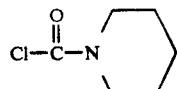
(41)

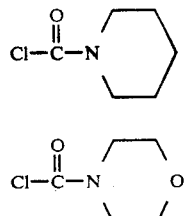
(42)

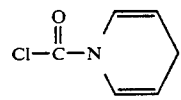
(43)

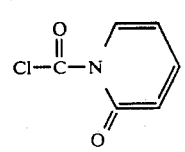
(44)

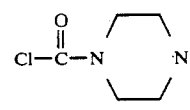
(45)

Cl—SO$_2$—CH$_3$ (46)

Cl—SO$_2$—CH$_2$CF$_3$ (47)

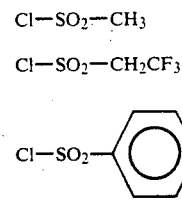
(48)

The method of activating the cellulosic membrane with the compound of the formula (I) or (II) is explained below in greater detail.

Activation of grains with a compound of the formula (I) is known (K. Nilsson & K. Mosbach, *Methods in Enzymology*, Vol. 104, 56 to 69 (1984)), in which fine agarose and cellulose grains are reacted with 4-toluenesulfonyl chloride or 2,2,2-trifluoroethanesulfonyl chloride at room temperature so as to activate the grains. However, activating a membrane with the same compound is not known.

Attempts were made to activate a cellulosic asymmetric membrane under the same reaction condition as that described in the above-cited reference but substantially nothing was activated. Accordingly, changes in the reaction conditions for activating the membrane were made and, as a result, it was found that the cellulosic membrane could be activated under the following reaction conditions. For instance, in the case of p-toluenesulfonyl chloride, about 100 ml of a solvent containing from 30 mmol to 0.7 mol, preferably from 0.3 to 0.5 mol, of p-toluenesulfonyl chloride and a base (for example, pyridine or triethylamine) in an amount of 1.5 equivalents of p-toluenesulfonyl chloride is added to 1 g of cellulosic membrane and then reacted at 20° to 80° C., preferably 40° to 60° C., for 15 minutes to 3 hours, preferably 1 to 2 hours, whereby the membrane can be activated. Suitably solvents usable in the reaction, are, for example, acetonitrile, pyridine, acetone, dioxane, N,N-dimethylformamide, diethylene glycol, diethyl ether and chloroform. In particular, a favorable result can be obtained when pyridine or acetonitrile is used as the solvent.

On the other hand, activation of grains with a compound of the formula (II) is also partly known (M. Wilchek et al, *Biochemistry International*, Vol. 4, 629 to 635 (1982)), in which fine agarose and cellulose grains are reacted with compounds of formulae:

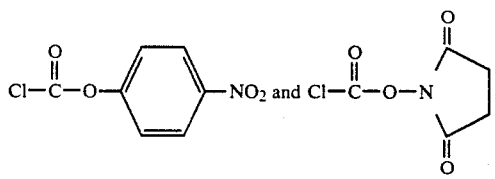

at a low temperature of 4° C. so as to activate the grains. However, activating a membrane with the same compounds is not known.

Activation of a cellulosic membrane under the same reaction conditions as that described in the above-cited reference was attempted but almost nothing was activated. Accordingly, changes in the reaction conditions for activating the membrane were made and, as a result, it was found that a cellulosic membrane could be activated under the following reaction conditions. Specifically, from 10 to 80 mmol of a compound of the formula (II) and from about 20 to 50 ml of a solvent are added to 1 g of a cellulosic membrane and then a base, such as pyridine or triethylamine, is added thereto. The amount of the base to be added is from 1 to 5 molar times, preferably from 1.5 to 3 molar times, of the compound of the formula (II) as used. The reaction is conducted at 10° to 80° C., preferably 40° to 60° C., for 15 to 90 minutes so as to activate the cellulosic membrane. Suitable solvents to be used in the reaction are, for example, acetonitrile, pyridine, acetone, dioxane, toluene, ethyl acetate and chloroform. The reaction methods thus discovered are markedly different from known methods particularly in the point of the reaction temperature, and in addition, the former are somewhat different from the latter from the standpoint of the reaction solvent to be used.

In using a compound of the formula (I), the amount of the active group introduced by the activation reaction can be measured by applying a known amount of β-phenethylamine to the activated membrane and determining the amount of the β-phenethylamine decreased because of the reaction thereof with the active group. It is desired for sufficient fixation of a physiologically active substance to the activated membrane that the active groups be introduced into the cellulosic membrane in a proportion of from 0.1 to 10 mol%, more preferably from 0.5 to 5 mol%, to the whole of glucose constituting the cellulosic membrane.

In using a compound of the formula (II), the amount of the active group introduced by the activation reaction can be measured by applying a known amount of an alkali to the activated membrane and determining the amount of the group released by reaction with the alkali. It is desired for sufficient fixation of a physiologically active substance to the activated membrane that the active groups be introduced into the cellulosic membrane in a proportion of from 0.1 to 10 mol%, more preferably from 0.5 to 5 mol%, to the whole of glucose constituting the cellulosic membrane.

The method of fixing a physiologically active substance to the activated cellulosic membrane is explained hereinafter.

First, the physiologically active substance to be fixed is dissolved in a buffer having a pH of from 6 to 9.5. The buffer to be employed in the process is preferably one not containing a primary amino group, for example, a phosphate buffer, a borate buffer, a morpholinoethanesulfonate (MES) buffer or a hydroxyethylpiperazineethanesulfonate (HEPES) buffer. If desired, a stabilizer for the physiologically active substance to be fixed may be added to the buffer. The resulting solution is applied to the celluolosic membrane under pressure, whereupon the solution is circulated and reacted with the cellulosic membrane at 4° to 40° C. for 1 to 12 hours. After completion of the fixation reaction, a buffer solution is applied to the membrane to wash the membrane. Further, an aqueous solution of an alkali or an amine such as ethanolamine is applied to the thus washed membrane, whereby the active groups remaining in the membrane are inactivated upon reaction therewith. Finally, the membrane is again washed with a buffer solution.

According to the above-mentioned method, a physiologically active substance is fixed to the cellulosic membrane.

Examples of physiologically active substances which can be fixed to the activated cellulosic membrane in accordance with the present invention include, for example, enzymes, coenzymes, antibodies, hormones, receptors, lectins, inhibitors, etc. Examples of enzymes are hydrolases such as trypsin, chymotrypsin, thermolysin, papain, asparaginase, lipase, amylase, cellulase, lysozyme and urease; oxido-reductases such as alcohol dehydrogenase, lactate dehydrogenase, glucose oxidase, aldehyde dehydrogenase, D-amino acid oxidase, peroxidase, catalase and superoxide dismutase; transferases such as hexokinase, creatine kinase and alanine transaminase; lyases such as fumarase, aspartate ammonia lyase, threonine aldolase and pyruvate decarboxylase; isomerases such as glucose phosphate isomerase and methylmalonyl CoA mutase; and ligases such as glutamine synthetase, acetyl CoA carboxylate and DNA ligase. Examples of other physiologically active substances which are employable in the present invention are coenzyme derivatives such as $N^6$-(6-aminohexyl)-AMP; bacterial Fc receptors such as protein A; immunoglobulins and Fab fragment thereof; lectins such as concanavalin A and wheat germ agglutinin; inhibitors such as soybean trypsin inhibitor; and amino acids such as phenylalanine, tryptophan and histidine.

It is extremely important for the physiologically active substance which is fixed to an activated carrier to be hardly deactivated on fixing the substance to the activated carrier and that the physiologically active substance fixed is not released from the carrier with the passage of time. In this respect, known methods for cellulosic membranes where the membrane is activated with an oxidizing agent or a triazine derivative still have various disadvantages to be overcome. In contrast, the cellulosic membrane activated by the method of the present invention has a high reactivity with various physiologically active substances. In addition, in accordance with one embodiment of the present invention, the physiologically active substance fixed to the activated cellulosic membrane is introduced into the membrane under pressure, for example, by the action of a pump, and therefore no extra time is not necessary for diffusing the substance into the membrane. As a result, for most physiologically active substances, fixation to the activated membrane is finished in a period of from 1 to several hours at 4° C. and a stable chemical bond between the substance and the membrane is thereby formed. Since the fixation of physiologically active substances can be completed in a short period of time in accordance with the method of the present invention as described above, a reduction in the physiological activity of the thus fixed substance is small, as opposed to the above-mentioned known methods where the fixation is effected under the condition of from 4° C. for 12 hours to 40° C. for one full day.

In addition, since the bonding site between the cellulosic membrane and the physiologically active substance in the fixed membrane of the present invention is hydrophilic but non-ionic, the fixed membrane is free from non-specific absorption of proteins and the like. Accordingly, the fixed membrane is suitable for applications as a sensor and as a material for affinity chromatography.

Furthermore, since the cellulosic membrane is resistant to almost all organic solvents, the physiologically active substance fixed by the present invention can be utilized in organic solvent systems.

The following examples are given to illustrate the present invention in greater detail but not to limit it in any way. Unless otherwise indicated, all parts, percents, ratios and the like are by weight.

EXAMPLE 1

Preparation of Activated Cellulosic Membrane with 2,2,2-Trifluoroethanesulfonyl Chloride 10 ml of acetone and 4 ml of pyridine were added to 150 cm$^2$ of cellulosic microfilter FR-40 (manufactured by Fuji Photo Film Co., Ltd.; pore diameter 0.4$\mu$). 2 ml of 2,2,2-trifluoroethanesulfonyl chloride was added dropwise thereto and then such was shaken at 40° C. for 30 minutes. Afterwards, the membrane was well washed with acetone and 1 mM hydrochloric acid in order and then stored at 4° C. Accordingly, a cellulosic membrane having active groups in an amount of 74 $\mu$mol/g was obtained.

EXAMPLE 2

Fixation of Thermolysin

The activated cellulosic membrane prepared in Example 1 was used.

50 mg of thermolysin was dissolved in 50 ml of 0.05 M morpholinoethanesulfonate buffer (pH 8.0) containing 5 mM CaCl$_2$. The resulting thermolysin solution was permeated into the activated cellulosic membrane set in a filter holder for filtration and circulated therethrough for 5 hours at 4° C. using a pump, whereby the thermolysin was fixed to the membrane. Next, in order to remove the remaining active groups, an aqueous 0.1 M ethanolamine solution was circulated through the membrane for 2 hours at 4° C. Finally, the buffer solution was permeated into the membrane to fully wash the same. The amount of enzyme as fixed to the membrane was measured by determining the amount of the enzyme remaining in the solution by UV-absorption method.

Determination of Activity

The substrate used was benzyloxycarbonyl-L-aspartyl-L-phenylalanine methyl ester (Z-aspartame), which was dissolved in 0.05 M N-2-hydroxyethyl-piperazine-N'-2-ethanesulfonate (HEPES) buffer (pH 7.0) in a concentration of 8 mM. The thermolysin-fixed membrane was placed in a filter holder for filtration, and the substrate solution was circulated through the membrane at 25° C. whereupon the concentration of the product (Z-aspartic acid) in the solution permeated into the membrane was determined. The result obtained is shown in Table 1 below.

COMPARATIVE EXAMPLE 1

Preparation of Thermolysin-Fixed Membrane by Activation Method with Oxidizing Agent FR-40 membrane was immersed in 0.5 M sodium metaperiodate and reacted therewith for 5 hours at 40° C. The membrane was washed with a pure water and then the same thermolysin solution as that used in Example 1 was circulated through the membrane for 5 hours at 4° C. so that the thermolysin was fixed to the membrane. Next, 1 mg/ml of sodium boronhydride was added to the enzyme solution and the resulting solution was circulated through the membrane for 2 hours at 4° C. Finally, the buffer solution was permeated into the membrane to fully wash the membrane. Activity determination was achieved in the same manner as that in Example 2. The result obtained is shown in Table 1 below.

TABLE 1

|  | Example 2 | Comparative Example 1 |
|---|---|---|
| Amount of Fixed Thermolysin | 22 mg/g(membrane) | 9 mg/g(membrane) |
| Relative Activity(*) of Fixed Thermolysin | 1.1 $\mu$mol/mg · min | 0.8 $\mu$mol/mg · min |

Note:
(*)Relative activity is represented by the amount of the substrate ($\mu$mol) decomposed by the enzyme (1 mg) per minute.

EXAMPLE 3

Preparation of Trypsin-Fixed Membrane: Activation 30 g of N-hydroxysuccinimidochloroformate and 100 ml of acetonitrile were added to 1200 cm$^2$ of cellulosic microfilter FR-40 (manufactured by Fuji Photo Film Co., Ltd.; pore diameter 0.4$\mu$). 30 ml of pyridine was added dropwise thereto with stirring under ice-cooling and successively such was shaken for 30 minutes at 40° C. Afterwards, the membrane was well washed with methanol and acetone in order and dried to obtain an activated cellulosic membrane.

Fixation of Trypsin 50 mg of trypsin was dissolved in 50 ml of HEPES buffer (pH 7.5) containing 5 mM CaCl$_2$. The resulting trypsin solution was permeated into the activated cellulosic membrane set in a filter holder for filtration and circulated therethrough for 5 hours at a rate of about 1 ml/min at a temperature of 4° C. using a pump, whereby the trypsin was fixed to the membrane. Next, to remove the remaining active groups, an aqueous 0.1 M ethanolamine solution was circulated through the membrane for 5 hours at 4° C. Finally, the buffer solution was permeated into the membrane so as to fully wash the membrane. The amount of enzyme fixed to the membrane was measured by determining the amount of enzyme remaining in the solution using a ninhydrin reaction.

Determination of Activity

The substrate used was L-benzoylarginineparanitroanilide (L-BAPA), which was dissolved in 0.05 M tris-buffer (pH 8.2) containing 10 mM $CaCl_2$, in a concentration of $10^{-4}$ M. The trypsin-fixed membrane was placed in a filter holder for filtration, and the substrate solution was permeated into the membrane at 25° C. whereupon the concentration of the product in the solution permeated into the membrane was determined. The result obtained is shown in Table 2 below.

COMPARATIVE EXAMPLE 2

Preparation of Trypsin-Fixed Membrane by Activation Method with Oxidizing Agent

FR-40 membrane was immersed in 0.5 M sodium metaperiodate and reacted therewith for 5 hours at 40° C. The membrane was washed with a pure water and then the same trypsin solution as used in Example 3 was circulated through the membrane for 5 hours at 4° C. so that the trypsin was fixed to the membrane.

Next, 1 mg/ml of sodium boronhydride was added to the enzyme solution and the resulting solution was circulated through the membrane for 2 hours at 4° C. The results obtained are shown in Table 2 below.

TABLE 2

|  | Example 3 | Comparative Example 2 |
|---|---|---|
| Amount of Fixed Trypsin | 3.0 mg/g(membrane) | 1.2 mg/g(membrane) |
| Relative Activity of Fixed Trypsin | 160 μmol/mg · min | 73 μmol/mg · min |

EXAMPLE 4

Preparation of IgG-Fixed Membrane

Activation 30 g of p-nitrophenyl chloroformate and 100 ml of acetonitrile were added to 1000 cm² of cellulosic microfilter FR-40. 30 ml of pyridine was added dropwise thereto with stirring under ice-cooling, and such was shaken at 40° C. for 30 minutes and reacted. Afterwards, the membrane was well washed with methanol and acetone in order and dried to obtain an activated cellulosic membrane.

Fixation of IgG 50 mg of rabbit anti-human IgG was dissolved in 50 ml of 0.05 M phosphate buffer (pH 7.4). This was fixed to the activated cellulosic membrane prepared as described above, in the same manner as in Example 3, and the amount of the anti-human IgG fixed was determined also in the same manner as in Example 3.

Determination of Activity 25 g mg of human IgG was dissolved in 100 ml of 0.05 M phosphate buffer (pH 7.0) and introduced into the fixed membrane using a pump. Next, the buffer was introduced thereinto to wash the membrane, and then 0.2 N acetic acid was introduced into the thus washed membrane to desorb the adsorbed human IgG therefrom. The amount of the human IgG thus desorbed was determined with $OD_{280}$. The result obtained is shown in Table 3 below.

TABLE 3

|  | IgG-Fixed Membrane |
|---|---|
| Amount of Anti-human IgG Fixed | 19 mg/g(membrane) |
| Human IgG Adsorbed | 16.7 mg/g(membrane) |
| Activity (Human IgG/Anti-human IgG) | 88% |

The same process was repeated, using bovine serum albumin, and the amount adsorbed was found to be 0.5 mg/g(membrane) or less.

While the invention has been described in detail and with reference to specific embodiments thereof, it will be apparent to one skilled in the art that various changes and modifications can be made therein without departing from the spirit and scope thereof.

What is claimed is:

1. A method for activating a membrane comprising cellulose as a main component, which method comprises reacting said membrane with a compound of formula (II):

wherein $R_1$ represents a releasing group, so as to be able to form a stable bond between the resulting activated membrane and a physiologically active substance when said activated membrane is reacted with said physiologically active substance, while retaining the activity of the resulting bound physiologically active substance.

2. The method as in claim 1, wherein said e membrane is an asymmetric membrane comprising cellulose as a main component and with a flat or hollow shape having a dense surface layer on one side of the membrane and having a relatively rough porous layer on the other side thereof.

3. The method as in claim 2, wherein said membrane is a porous microfilter having a pore diameter of from 0.1μ to 10μ.

4. The method as in claim 2, wherein said membrane is an ultrafilter membrane having a pore diameter of from 1,000 to 1,000,000 for fractionating by molecular weight.

5. A method of fixing a physiologically active substance on the activated membrane of claim 2, comprising reacting the physiologically active substance and the membrane.

6. The method as in claim 5, wherein the physiologically active substance is selected from the group consisting of enzymes, coenzymes, antibodies, hormones, receptors, lectins and inhibitors.

7. A physiologically active substance-fixed membrane obtained by the method as claimed in claim 5.

8. The method as in claim 1, wherein the compound of formula (II) is a compound represented by the following formula (III) or (IV):

-continued

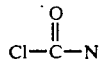
(IV)

where $R_2$ represents an alkyl group, an aryl group or a heterocyclic group, each of which may be substituted and which is released as $^\ominus OR_2$, and X represents a nonmetallic atomic group for forming a 5-membered or 6-membered ring together with the nitrogen atom in the formula.

9. An activated membrane obtained by the method as claimed in claim 1.

10. The method as claimed in claim 1, wherein from 10 to 80 mmol of a compound of formula (II) and from 20 to 50 ml of a solvent are added to 1 g of cellulosic membrane, and then a base is added thereto, wherein the amount of base added is from 1 to 5 molar times the amount of the compound of formula (II), and wherein the reaction is conducted at 10° to 80° C. for 15 to 90 minutes.

11. The method as claimed in claim 10, wherein the amount of said base is 1.5 to 3 molar times the amount of the compound of formula (II) and the reaction is conducted at 40° to 60° C.

12. The method as claimed in claim 10, wherein said solvent is selected from the group consisting of acetonitrile, pyridine, acetone, dioxane, toluene, ethyl acetate and chloroform.

13. The method as claimed in claim 10, wherein said base is selected from the group consisting of pyridine and triethylamine.

* * * * *